(12) United States Patent
Hawthorne et al.

(10) Patent No.: US 8,741,250 B2
(45) Date of Patent: Jun. 3, 2014

(54) HYDROXYLATION OF ICOSAHEDRAL BORON COMPOUNDS

(75) Inventors: M. Frederick Hawthorne, Columbia, MO (US); Oleg Bondarev, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 136 days.

(21) Appl. No.: 13/566,789

(22) Filed: Aug. 3, 2012

(65) Prior Publication Data
US 2013/0078175 A1  Mar. 28, 2013

Related U.S. Application Data

(60) Provisional application No. 61/574,602, filed on Aug. 5, 2011.

(51) Int. Cl.
*C01B 35/10* (2006.01)
*C07F 5/02* (2006.01)

(52) U.S. Cl.
CPC .. *C01B 35/10* (2013.01); *C07F 5/02* (2013.01)
USPC ............................................. 423/277; 568/5

(58) Field of Classification Search
CPC ................................. C01B 35/10; C01B 35/08
USPC ................................... 423/276, 277; 568/4, 5
See application file for complete search history.

(56) References Cited

U.S. PATENT DOCUMENTS

| | | |
|---|---|---|
| 5,306,855 A | 4/1994 | Periana |
| 6,323,372 B1 | 11/2001 | Hawthorne |
| 6,392,068 B1 | 5/2002 | Lu |
| 6,664,426 B1 | 12/2003 | Hawthorne |
| 7,320,993 B1 | 1/2008 | Biedermann |
| 2008/0102026 A1 | 5/2008 | Lee |

FOREIGN PATENT DOCUMENTS

| | | |
|---|---|---|
| WO | 9850333 A1 | 11/1998 |
| WO | 2013040222 A1 | 3/2013 |
| WO | 2013082150 A1 | 6/2013 |

OTHER PUBLICATIONS

Peymann, Aromatic Polyhedral Hydroxyborates: Bridging Boron Oxides and Boron Hydrides, Angew. Chem. 1999, 111, 1129-1132; Angew. Chem. Int. Ed 1999, 38, 1061-1064.
Peymann, Dodecahydroxy-closo-dodecaborate(2-), J. Am. Chem. Soc. 2001, 123, 2182-2185.
Bayer, An Improved Method for the Synthesis of [closo-B12(OH)12]-2, Inorg Chem. 2004, 43, 2018-2020.
Maderna, Twelvefold Functionalization of an Icosahedral Surface by Total Esterification of [B12(OH)12]12-: 12(12)- Closomers, Angew. Chem. 2001, 113, 1709-1712; Angew. Chem. Mt. Ed 2001, 40, 1662-1664.
Peymann, Dodeca(benzyloxy)dodecaborane, B12(OCH2Ph)12: A Stable Derivative of hypercloso-B12H12, Angew. Chem. 2001, 113, 1713-1715; Angew. Chem. Int. Ed. 2001, 40, 1664-1667.
Farha, Synthesis of Stable Dodecaalkoxy Derivatives of hypercloso-B12H12, J. Am. Chem. Soc. 2005, 127, 18243-18251.
Li, Organic Syntheses on an Icosahedral Borane Surface: Closomer Structures with Twelvefold Functionality, J. Am. Chem. Soc. 2005, 127, 17832-17841.

(Continued)

*Primary Examiner* — Anthony J Zimmer
*Assistant Examiner* — Justin Bova
(74) *Attorney, Agent, or Firm* — Polsinelli PC

(57) ABSTRACT

The present invention relates to a synthetic method for producing a per-hydroxylated icosahedral boron compound via catalytic hydroxylation of icosahedral boron compound using a soft electrophile.

25 Claims, 13 Drawing Sheets

(56) References Cited

OTHER PUBLICATIONS

Lee, Alkoxy Derivatives of Dodecaborate: Discrete Nanomolecular Ions with Tunable Pseudometallic Properties, Angew. Chem. 2007, 119, 3078-3082; Angew. Chem. Mt. Ed. 2007, 46, 3018-3022.

Peer, Nanocarriers as an emerging platform for cancer therapy, Nature Nanotechnology 2007, 2, 751-760.

Caravan, Gadolinium(III) Chelates as MRI Contrast Agents: Structure, Dynamics, and Applications, Chem. Rev. 1999, 99, 2293-2352.

Weiner, Metallic Radionuclides: Applications in Diagnostic and Therapeutic Nuclear Medicine, Radiochimica Acta 1995, 70/71, 273-288.

Buchsbaum, Experimental Tumor Targeting with Radiolabeled Ligands, Cancer 1997, 80, 2371-2377.

Hawthorne, Applications of Radiolabeled Boron Clusters to the Diagnosis and Treatment of Cancer, Chem. Rev. 1999, 99, 3421-3434.

Peyman, A Study of the Sequential Acid-Catalyzed Hydroxylation of Dodecahydro-closo-dodecaborate(2-), Inorg. Chem. 2000, 39, 1163-1170.

Periana, Platinum Catalysts for the High-Yield Oxidation of Methane to a Methanol Derivative, Science 1998, 280, 560-564.

Periana, High yield conversion of methane to methyl bisulfate catalyzed by iodine cations, Chem. Commun. 2002, 2376-2377.

Zerella, Methane oxidation to acetic acid catalyzed by Pd2+ cations in the presence of oxygen, J. Catal. 2006, 237, 111-117.

Zerella, Direct oxidation of methane to acetic acid catalyzed by Pd2+ and Cu2+ in the presence of molecular oxygen, Chem. Commun. 2004, 1948-1949.

Jiang, Iodination Reactions of Icosahedral para-Carborane and the Synthesis of Carborane Derivatives with Boron-Carbon Bonds, Inorg. Chem. 1995, 34, 3491-3498.

Zheng, Facile Electrophilic Iodination of Icosahedral Carboranes. Synthesis of Carborane Derivatives with Boron-Carbon Bonds via the Palladium-Catalyzed Reaction of Diiodocarboranes with Grignard Reagents, Inorg. Chem. 1995, 34, 2095-2100.

Jiang, Palladium-Catalyzed Coupling of Ethynylated p-Carborane Derivatives: Synthesis and Structural Characterization of Modular Ethynylated p-Carborane Molecules, Inorg. Chem. 1996, 35, 4355-4359.

Peymann, Synthesis of Alkyl and Aryl Derivatives of closo-B12H12 2- by the Palladium-Catalyzed Coupling of closo-B12H11I2-with Grignard Reagents, Inorg. Chem. 1998, 37, 1544-1578.

Periana, Perspectives on some challenges and approaches for developing the next generation of selective, low temperature, oxidation catalysts for alkane hydroxylation based on the CH activation reaction, J. Mol. Catal. A 2004, 220, 7-25.

Periana, A Mercury-Catalyzed, High-Yield System for the Oxidation of Methane to Methanol, Science 1993, 259, 340-343.

International Search Report and Written Opinion from related international application No. PCT/US2012/055181.

International Search Report and Written Opinion from related international application No. PCT/US2012/066849.

Valliant, The Medicinal Chemistry of Carboranes, Coordination Chemistry Reviews, 2002, pp. 173-230, vol. 232.

Sevryugina, Novel Approach to AmInocarboranes by Mild Amidation of Selected Iodo-carboranes, Inorg. Chem., 2010, pp. 10627-10634, vol. 49(22).

Ujvary, Synthesis of (s)-3-(1-hydroxy-p-carboran-12-yl)alanine, a novel hydrophobic tyrosine-memetic for peptides, Peptides, 2002, pp. 795-799, vol. 23.

Yoo, The First Stable Platinum(ii) Complex of a o-Carborane-linked Bipyridine as a Potential BNCT Reagent, Bull. Korean Chem. Soc., 2005, pp. 231-232, vol. 26(2).

Hasmann, FK866, Highly Specific Noncompetitive Inhibitor of Nicotinamide Phosphoribosyltransferase, Represents a Novel Mechanism for Induction of Tumor Cell Apoptosis, Cancer Res, 2003, pp. 7436-7442, vol. 63.

HYDROXYLATION OF ICOSAHEDRAL BORON COMPOUNDS

CROSS-REFERENCE TO RELATED APPLICATIONS

This application claims the priority of U.S. Provisional Application No. 61/574,602 filed Aug. 5, 2011, which is hereby incorporated by reference in its entirety.

FIELD OF THE INVENTION

The present invention relates to a synthetic method to produce per-hydroxylated icosahedral boron compounds and to compositions found on its synthetic pathway. More specifically, the method involves hydroxylation of an icosahedral boron compound using soft electrophiles and a sulfonic acid.

BACKGROUND

The ability to produce per-hydroxylated icosahedral boron compounds opens up a new field of boron cluster chemistry where the aromatic icosahedral cluster functions as the scaffolding for reactions performed on its oxygen sheathing. For example, $Cs_2[closo-B_{12}(OH)_{12}]$ can be used as the central core for the formation of dodeca-substituted monodisperse organic and inorganic compounds known as closomers, which are distinguished from dendrimers. The spacing of the per-hydroxylated icosahedral boron is reflected in the closomer species derived from it by simple organic reactions, which are characteristic for the hydroxyl group including carboxylate ester and alkyl ether formation. The resulting closomers may have spaced radial substituents of chosen size, hydrophilicity, ionic charge. Thus, the closomers display functions derived from their collected passenger molecules. Applications of these compounds may involve the development of chemical strategies making possible the synthesis of clusters in which the vertices become the anchoring site for a predetermined function. Such functions include, but are not limited to, tumor cell targeting moieties, gadolinium chelators from MRI contrast agents, plasma membrane penetrators, radionuclide chelators for diagnosis or therapy, fluorophores, chemotherapeutics, targeting and therapeutic peptides, carbohydrates and glycobiologics, synthetic antigens, RNA and DNA segments, immunoproteins, etc.

Current synthetic pathways to per-hydroxylated icosahedral boron compounds employ acid-catalyzed hydroxylation of icosahedral boron compound requiring the use of an $H_2O_2$ oxidant. However, the $H_2O_2$ oxidant poses increased risk of explosive oxidation of the $B_{12}^{2-}$ cage. Risk of explosive oxidation makes scaling reactions to a higher volume particularly unattractive.

Therefore, there is a need for improved synthetic routes to per-hydroxylated icosahedral boron compounds.

SUMMARY

In one aspect, the present disclosure provides a method for producing a per-hydroxylated icosahedral boron, wherein the method comprises contacting an icosahedral boron compound with a soft electrophile and a sulfonic acid to form a sulfonated intermediate and hydrolyzing the sulfonated intermediate to give per-hydroxylated icosahedral boron.

In another aspect, the present disclosure provides a composition comprising $[closo-B_{12}(OSO_3R^1)_{12}]$, wherein $R^1$ is chosen from hydrocarbyl, substituted hydrocarbyl, hydrogen, or is not present such that the sulfonated intermediate is anionic.

In still another aspect, the present disclosure provides a method of producing $[closo-B_{12}(OH)_{12}]^{2-}$, wherein the method comprises contacting $[closo-B_{12}H_{12}]^{2-}$ with about 0.5 mol % to about 5 mol % of a soft electrophile chosen from a palladium species, a platinum species, and an iodine species, with sulfuric acid such that a sulfonated intermediate is formed; and then hydrolyzing the sulfonated intermediate to give $[closo-B_{12}(OH)_{12}]^{2-}$.

Other features and iterations of the disclosure are described in more detail herein.

DETAILED DESCRIPTION OF INVENTION

Figure 1:
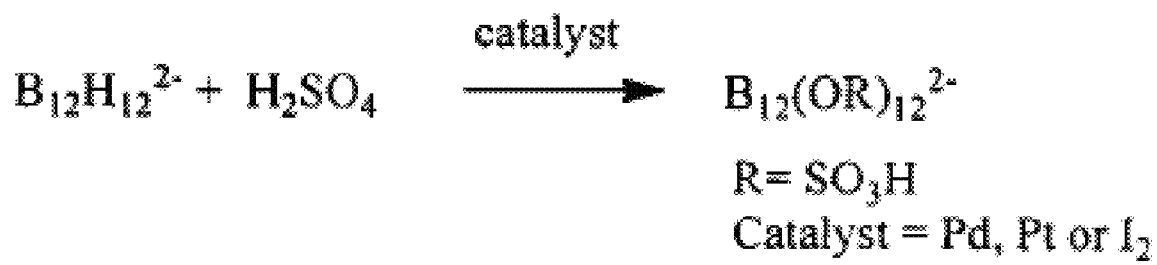
FIG. 1 is a two-step synthetic scheme to produce $[closo-B_{12}(OH)_{12}]^{2-}$ through the catalytic hydroxylation of $[closo-B_{12}H_{12}]^{2-}$ with soft electrophiles.
Figure 1:
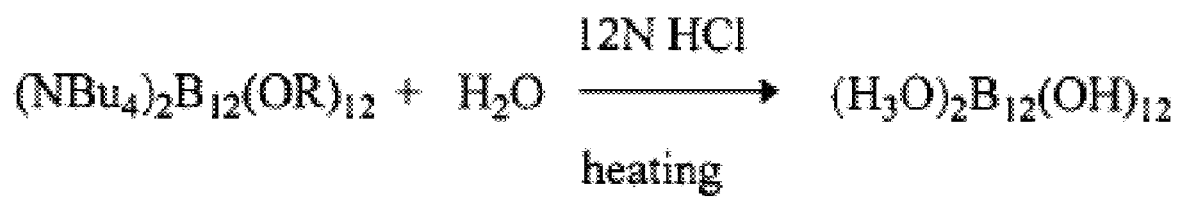
Figure 2:
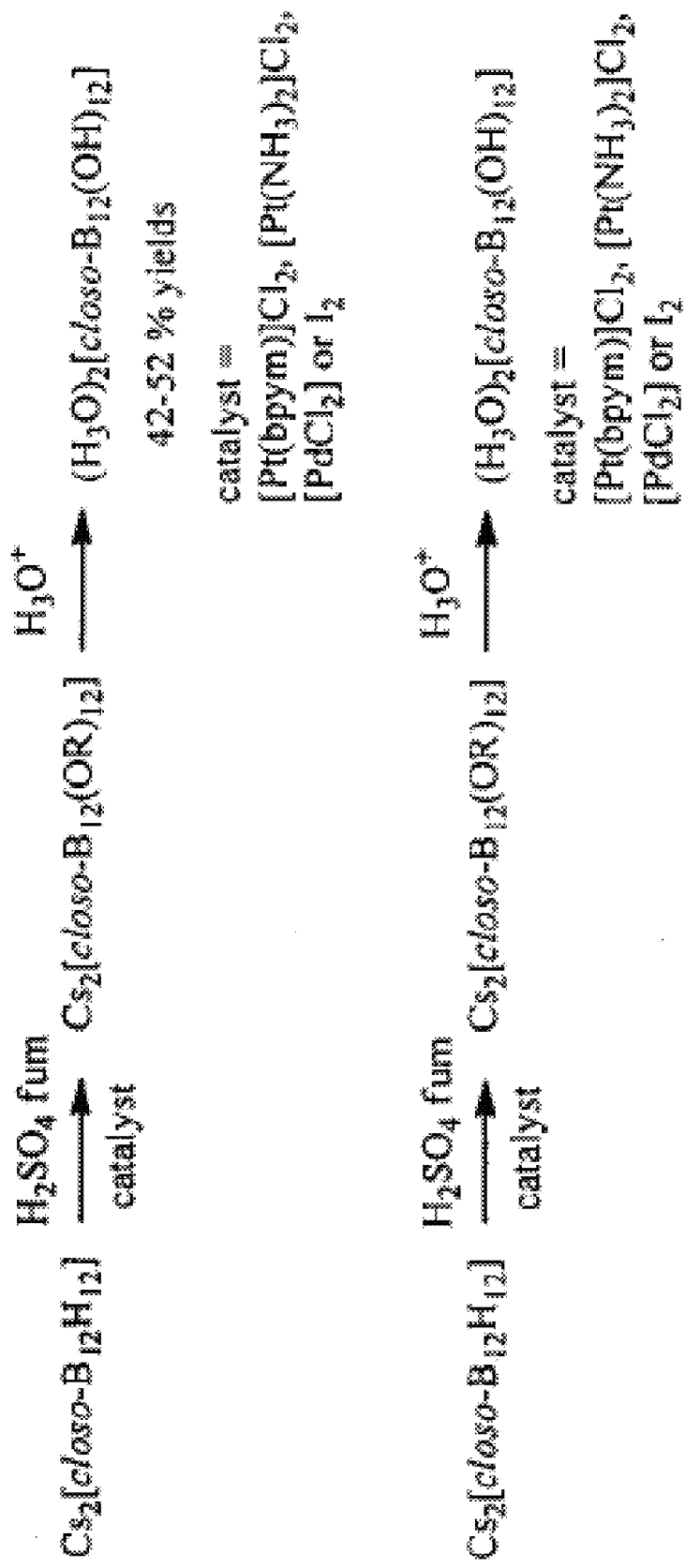
FIG. 2 is a two-step, one-pot synthetic scheme to produce $[closo-B_{12}(OH)_{12}]^{2-}$ through the catalytic hydroxylation of $[closo-B_{12}H_{12}]^{2-}$ with soft electrophiles.
Figure 3A:
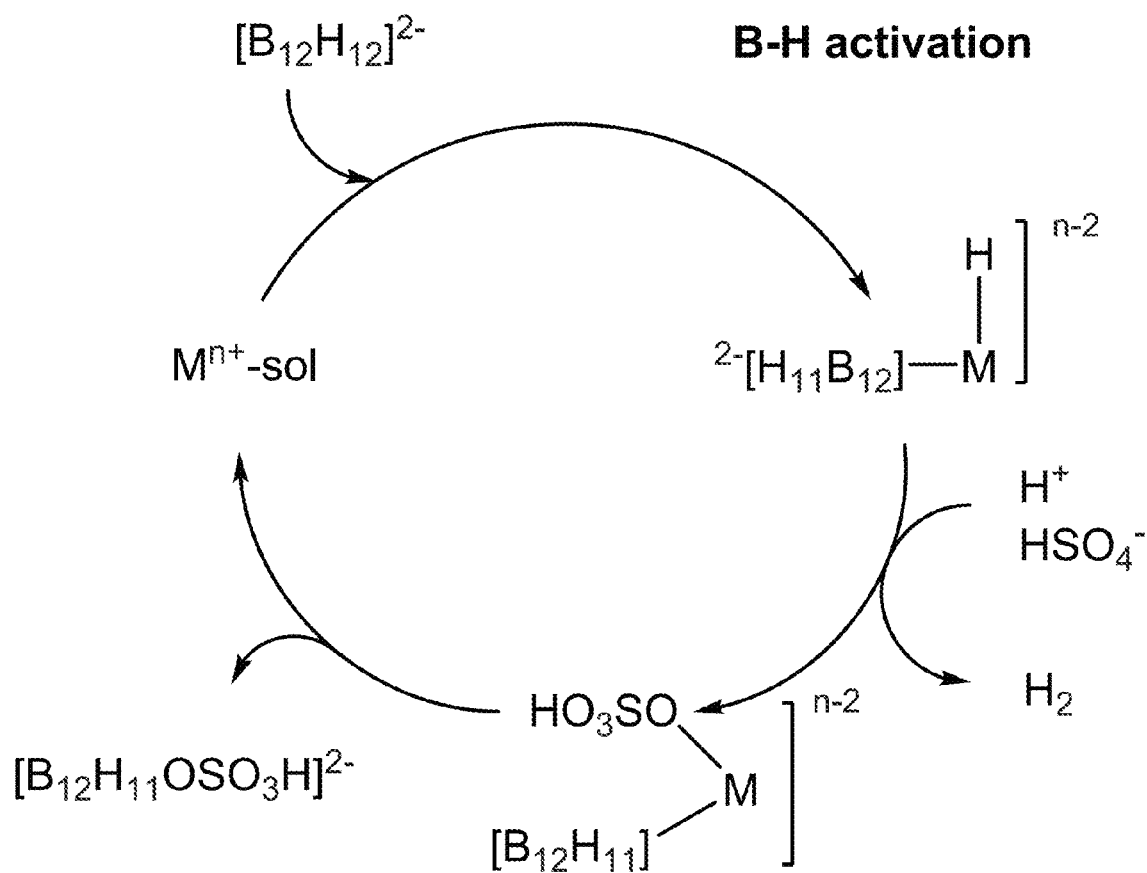
FIG. 3(A) is the proposed soft electrophile-catalyzed mechanism. The soft electrophile-catalyzed B—H activation may proceed via oxidative addition of the catalyst center, M, to a B—H vertex which results in the formation of an H-M-B-intermediate. Subsequent reductive elimination of the coupled product and regeneration of catalytically active electrophilic species completes the catalytic cycle. The reaction may proceed via solvated electrophilic species.
Figure 3B:
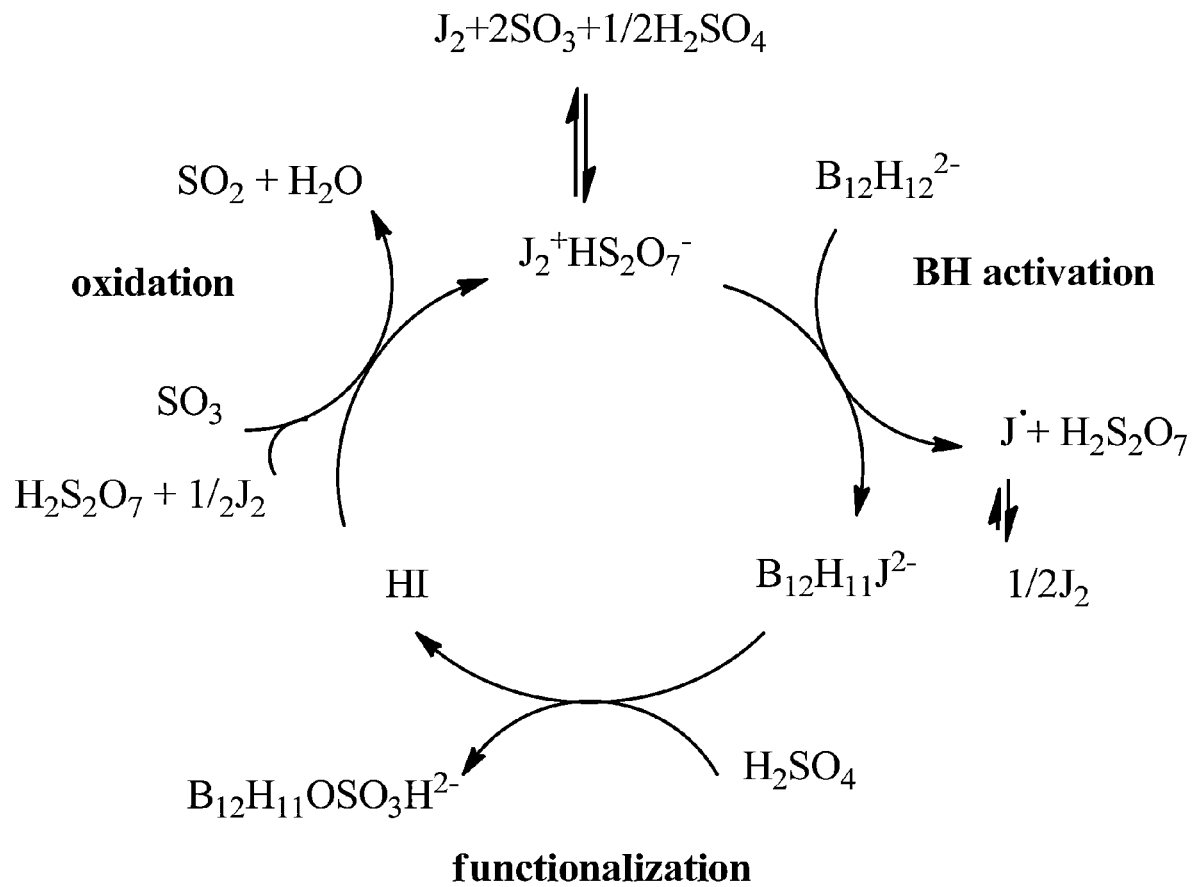
FIG. 3(B) shows a proposed cycle for iodine.

Briefly, therefore, the present invention relates to a synthesis and compounds on a pathway to per-hydroxylated icosahedral boron compounds. The synthesis is a safer process compared to the existing method and may be carried out in a one-pot reaction. The reaction is capable of scaling up with less risk of explosive oxidation of a boron cage species. In general, the synthesis involves contacting an icosahedral boron compound with a soft electrophile and sulfonic acid to produce a sulfonated intermediate. A per-hydroxylated boron compound is given with hydrolysis of the sulfonated intermediate.

(I) Methods of Producing Per-Hydroxylated Icosahedral Boron Compounds

In general, the synthesis involves contacting an icosahedral boron compound with a soft electrophile and sulfonic acid to produce a sulfonated intermediate. The per-hydroxylated icosahedral boron compound is given with hydrolysis of the sulfonated intermediate.

(a) Step (a)

Step (a) of the reaction involves contacting an icosahedral boron compound with a soft electrophile and a sulfonic acid. Icosahedral boron comprises an icosahedral structure with twelve vertexes. The icosahedral boron compound is the reactant and has boron-hydrogen bonds. For example, in [closo-$B_{12}H_{12}]^{2-}$ each vertex in is a boron atom which is further bonded to a hydrogen atom. The overall structure has a 2-charge and is generally found as a salt of one or more positively charged species. As used herein, an icosahedral boron compound may refer to either the ion or to any of its salts. [closo-$B_{12}H_{12}]^{2-}$ can be synthesized or purchased. For example $Cs_2$[closo-$B_{12}H_{12}$] may be purchased from BASF SE. Through the processes described herein, the boron-hydrogen bonds of the icosahedral boron compound, the reactant, are transformed to boron-hydroxy bonds. This transformation is described as hydroxylation.

(i) Soft Electrophile

The method provides that the icosahedral boron compound is contacted with a soft electrophile. Soft electrophiles are known in the art. Generally, soft electrophiles are characterized by a low LUMO (lowest unoccupied molecular orbital) and are generally polarizable and of low electronegativity. Without being bound to any particular theory, it is thought that the soft electrophile provides activation of the boron-hydrogen bonds of the icosahedral boron compound.

In some aspects, the soft electrophile comprises an iodine species. The iodine species may be from a variety of iodine containing sources including, by way of non-limiting example, alkyl iodides, metal iodides, molecular iodine. In some aspects, the iodine species may be $I_2$ or cationic iodine.

In another aspect the soft electrophile is a metal. The metal may be selected from Pt, Pd, Rh, Ir, Ru, Au, Ag, Hg, and Os or mixtures thereof. Preferred metals include Pt and Pd. In some aspects the metal is stabilized with one or more ligands which form mono-dentate or poly-dentate ligand complex with the metal. Thus, the mono-dentate or poly-dentate, bi-dentate, ligand employed in the catalyst complex may be a carbon or heteroatom-containing ligand which binds the metal through one or more carbon, nitrogen, sulfur or phosphorus atoms or mixtures thereof—e.g., phosphines, organo-phosphorus compounds, amines and heterocyclic organic compounds containing ring nitrogens and/or sulfur atoms.

In one aspect, the metal is on the general formal $MX_n$. M is a metal, X is an anion selected from halide, hydroxide, sulfate, bisulfate, nitrate and phosphate, and ammonia. Depending on the oxidation state of the metal n is an integer from 1 to 4. In some embodiments, M is Pd. In one preferred embodiment, the catalyst is [$PdCl_2$].

In still another aspect, the metal employed is a platinum or palladium metal ligand complex of the formula $ML_mX_n$ wherein M is the metal and L is a ligand. Ligands may be selected from mono-dentate or poly-dentate, bi-dentate, ligands. Ligands which bind the metal through one or more carbon nitrogen, sulfur or phosphorus atoms or mixtures thereof—e.g., phosphines, organo-phosphorus compounds, amines and heterocyclic organic compounds containing ring nitrogens and/or sulfur atoms may be used. X is an anion selected from halide, hydroxide, sulfate, bisulfate, nitrate and phosphate, and ammonia. Generally, m is 1 or 2, and n is an integer of 1 to 8 depending on the oxidation state of the metal employed. When M is platinum, X is preferably 1, 2, 3 or 4 and, most preferably, 1 or 2. In one preferred embodiment, the catalyst is $Pt(NH_3)_2Cl_2$.

In another aspect, the metal comprises a bipyrimidyl (bpym) ligand having the following structures, wherein $R^3$ and $R^4$ are independently selected from hydrogen, hydrocarbyl and substituted hydrocarbyl. In a preferred embodiment, $R^3$ and $R^4$ are hydrogen.

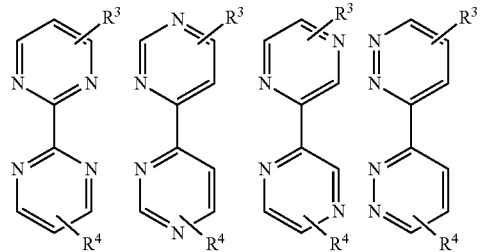

An exemplary soft electrophile which comprises the bipyrimidyl ligand is Pt(bpym)$Cl_2$, (dichloro-{2,2'-bipyrimidyl}platinum(II)).

The soft electrophile may be added to the reaction in catalytic amounts. In some aspects, the soft electrophile is provided in amounts ranging from 0.1 mol % to 10 mol % to the icosahedral boron reactant. In another embodiment, the soft electrophile is added in an amount ranging from 0.5 mol % to about 5 mol % to [closo-$B_{12}H_{12}]^{2-}$. In various embodiments, the soft electrophile is added to the reaction in an amount of about 0.5 mol %, about 1 mol %, about 1.5 mol %, about 2 mol %, about 2.5 mol %, about 3.0 mol %, about 3.5 mol %, about 4 mol %, about 4.5 mol %, or about 5 mol % to the icosahedral boron compound.

The catalysts are synthesized as has been described in the literature and is provided in more detail in the Examples.

(ii) Sulfonic Acid

Either in sequence or concurrently with the soft electrophile, icosahedral boron compound is contacted with a sulfonic acid.

Sulfonic acids are sulfur compounds of the general formula $R^1(S=O)_2OH$. For various acids $R^1$ may be selected from hydrocarbyl, substituted hydrocarbyl, hydrogen or may not be present such that a negative charge is present. Exemplary sulfonic acids methanesulfonic acid, toluenesulfonic acid, and sulfuric acid. In a preferred embodiment, $R^1$ is hydrogen and the sulfonic acid is sulfuric acid.

Sulfonic acids may be provided in a variety of concentrations. Concentrated acids have a concentration of about 18M. Lower concentration acids may also be used including, without limitation, 1M solutions, 5M solutions, 10M solutions and 14M solutions. Generally, lower concentration acids are provided as an aqueous solution. In one embodiment, concentrated sulfuric acid is provided to the reaction in step (a). In a particularly preferred embodiment, $H_2SO_4$ oleum with 2-30% $SO_3$ is added in step (a).

In general, the sulfonic acid may be provided in excess to the icosahedral boron compound and in various embodiments may provide the solvent for the reaction. In some embodiments, the weight to weight ratio of the icosahedral boron compound to the sulfonic acid can range from about 1:1 to about 1:100. In some embodiments, the weight to weight ratio of the icosahedral boron compound to sulfonic acid is about 1:5, about 1:10, about 1:15, about 1:20, about 1:25, about 1:30, about 1:35, about 1:40, about 1:50 or higher.

(iii) Reaction Conditions

The reaction temperature may vary in step (a) depending on the size of the reaction and catalyst loading. Step (a) may be conducted at a temperature ranging range from about 110° C. to about 220° C. In another embodiment, the range may be from about 160° C. to about 200° C. In some embodiments, step (a) is conducted at about 160° C., about 165° C., about 170° C., about 175° C., about 180° C., 185° C., about 190° C., about 195° C., about 200° C., about 205° C., about 210° C., about 215° C., or about 220° C.

The amount of time over which step (a) is conducted may also vary within various embodiments. In some embodiments, step (a) may be conducted over a period of 10 hours to 5 days. In other embodiments, step (a) may be conducted over a period of about 12 hours to about 2 days. In various embodiments, the reaction may be conducted over a period of about 12 hours, about 14 hours, about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours.

In one aspect of the invention, step (a) is conducted without the presence of an oxidizing agent. In one aspect, step (a) of the reaction is conducted without the presence of a reactive oxygen species. For example, step (a) of the reaction may be conducted in the absence of an $H_2O_2$ oxidizing agent or a reactive oxygen species produced from $H_2O_2$.

(b) Step (b)

Step (a) results in a sulfonated intermediate which is described in more detail in part (III). The method comprises hydrolyzing this sulfonated intermediate, to form the per-hydroxylated icosahedral boron compound in step (b).

Hydrolysis of the sulfonated intermediate can be performed by any method for hydrolyzing that is known in the art. In particular, hydrolysis can be performed with addition of water, an acid, a base, or a reducing agent.

In some aspects, hydrolysis is achieved with addition of water. In other aspects, an acid is provided. Water may be provided to the reaction as liquid or ice. When an acid is used, strong acid are preferred. Strong acids include without limitation hydrochloric acid, nitric acid, sulfuric acid, hydrobromic acid, hydroiodic acid, and perchloric acid. Generally, the water, ice, or acid may be added in excess to the theoretical amount of sulfonated intermediate.

Conditions for the hydrolysis reaction can vary. In general, heat is provided to achieve hydrolysis of the sulfonated intermediate. In some aspects, the reaction mixture is heated at reflux. In other aspects, the hydrolysis is performed in an autoclave.

The reaction temperature may vary in step (b) depending on the size of the reaction and the conditions. Step (b) may be conducted at a temperature ranging range from about 140° C. to about 220° C. In another embodiment, the range may be from about 160° C. to about 200° C. In some embodiments, step (b) may be conducted at about 160° C., about 165° C., about 170° C., about 175° C., about 180° C., 185° C., about 190° C., or about 195° C.

The amount of time over which step (b) is conducted may also vary within various embodiments. In some embodiments, step (b) may be conducted over a period of 10 hours to 5 days. In other embodiments, step (b) may be conducted over a period of about 12 hours to about 2 days. In various embodiments, the reaction may be conducted over a period of about 12 hours, about 14 hours, about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours.

In one aspect, the method can be performed in a single reaction vessel or as a one pot reaction. As used herein, a one pot reaction refers to a reaction that can be conducted by sequential addition of reagents into a reaction vessel without the isolation of intermediates. One pot reactions provide advantages in yield as purification steps and loss of product are unnecessary, and also provide numerous advantages in terms of scalability.

The per-hydroxylated icosahedral boron compound can be isolated from the reaction mixture using typical synthetic procedures. A per-hydroxylated icosahedral boron is an icosahedral compound where all available vertex positions are hydroxylated. Hydrolysis under acid conditions generally gives the product as the hydronium ion, which can be recovered by precipitation and filtration, techniques understood in the art.

A purification method for $(H_3O)_2[closo-B_{12}(OH)_{12}]$ is also provided based on the unusually low water solubility of $[closo-B_{12}(OH)_{12}]^{2-}$ alkali metal salts. Specifically, $(H_3O)_2[closo-B_{12}(OH)_{12}]$ may be converted to $Cs_2[closo-B_{12}(OH)_{12}]$ by the addition of $Cs_2CO_3$ and then recrystallized from water.

Figure 4:
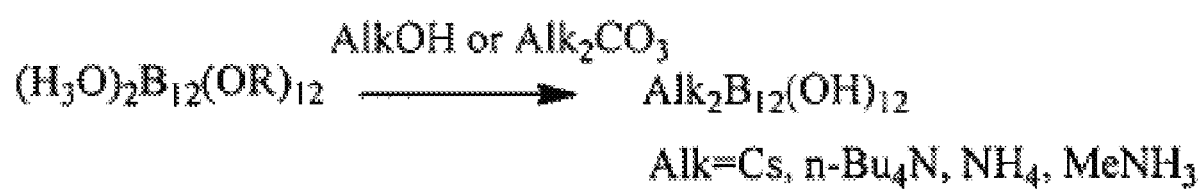
FIG. 4 is the synthetic scheme for production of $Alk_2B_{12}(OH)_{12}$.
Figure 5:
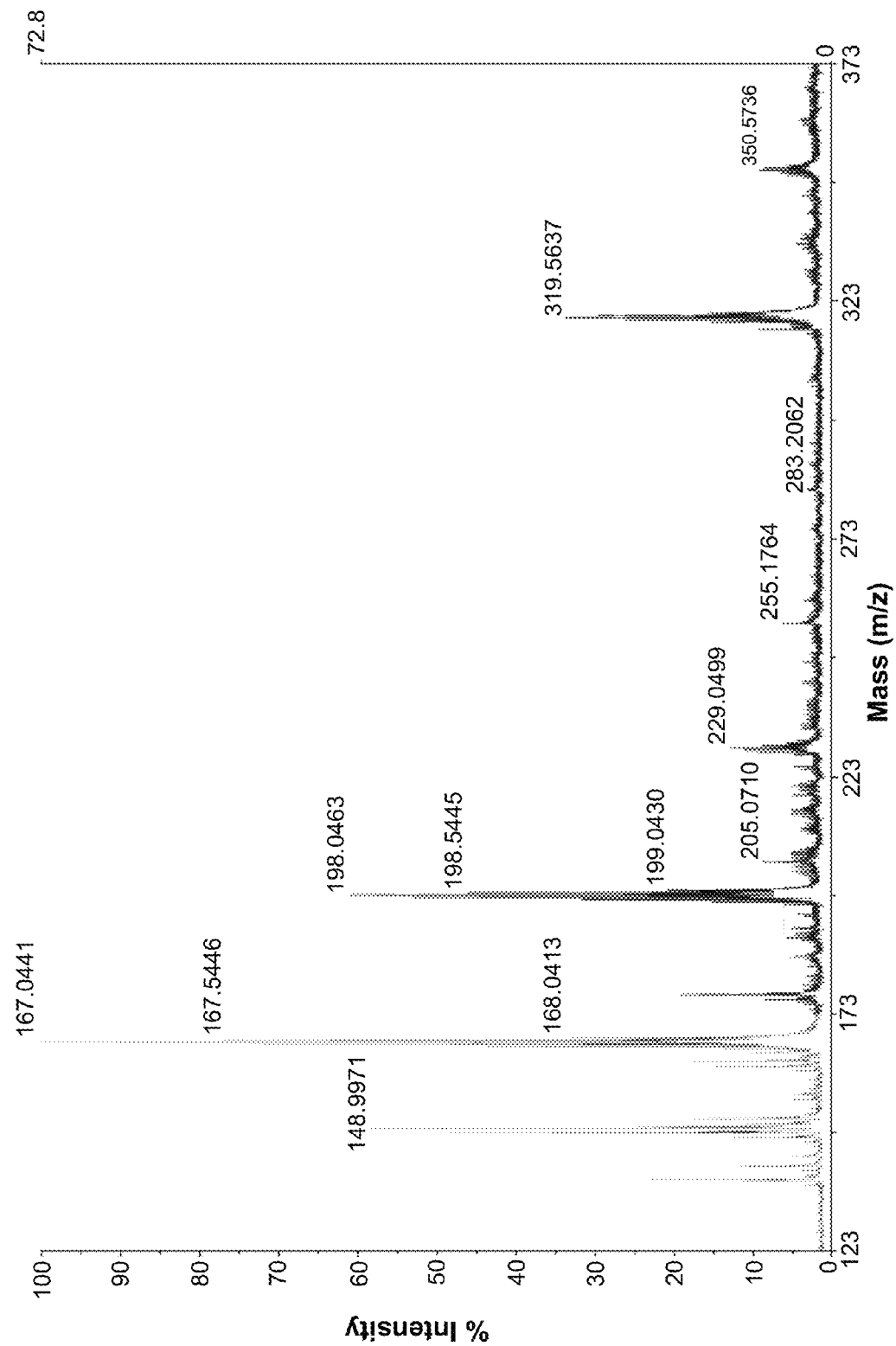
FIG. 5 is the ESI-MS negative ion mass spectrum of $Cs_2[closo-B_{12}(OSO_3H)12]$ mixture.
Figure 6:
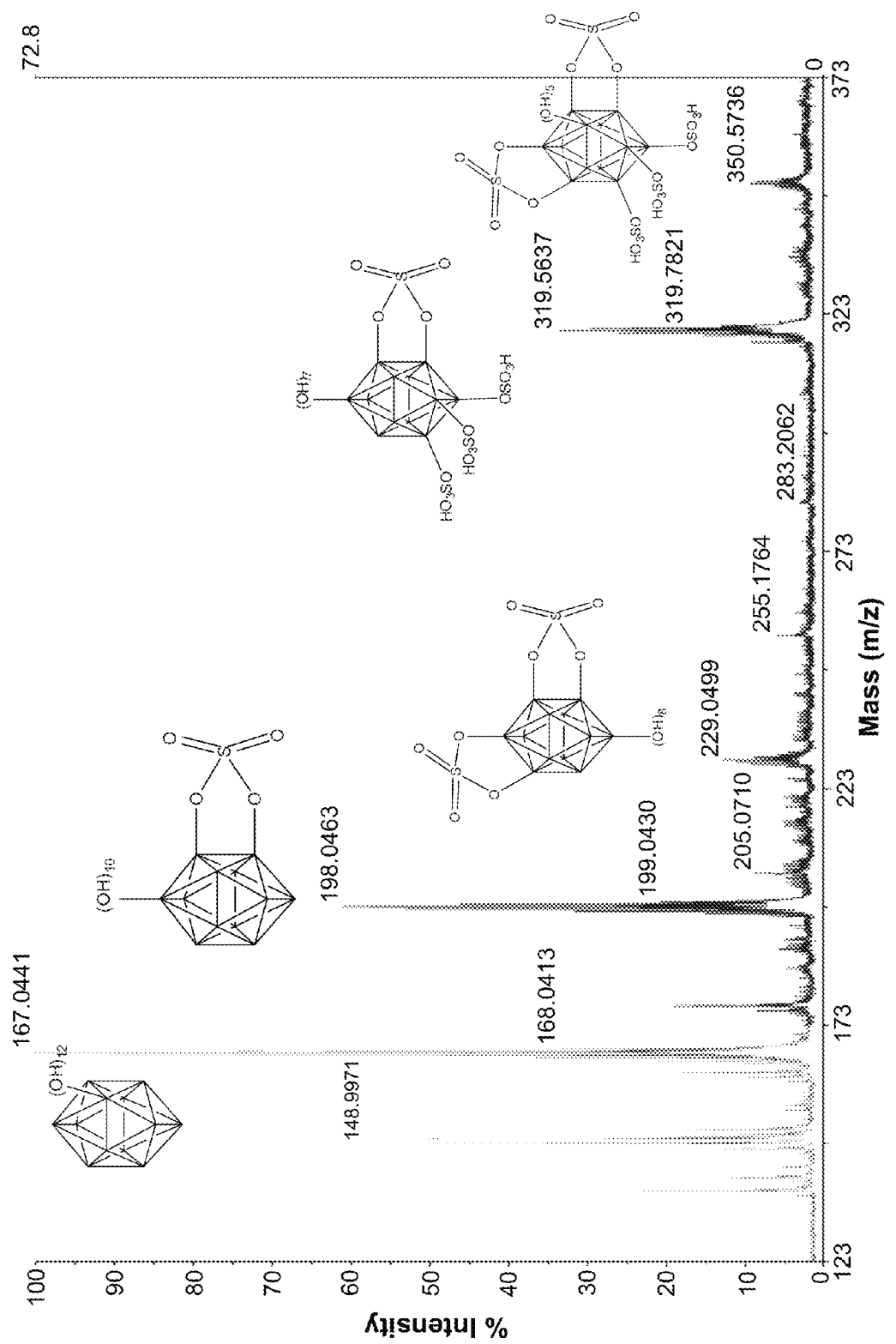
FIG. 6 is the ESI-MS negative ion mass spectrum of $Cs_2[closo-B_{12}(OSO_3H)12]$ mixture.
Figure 7:
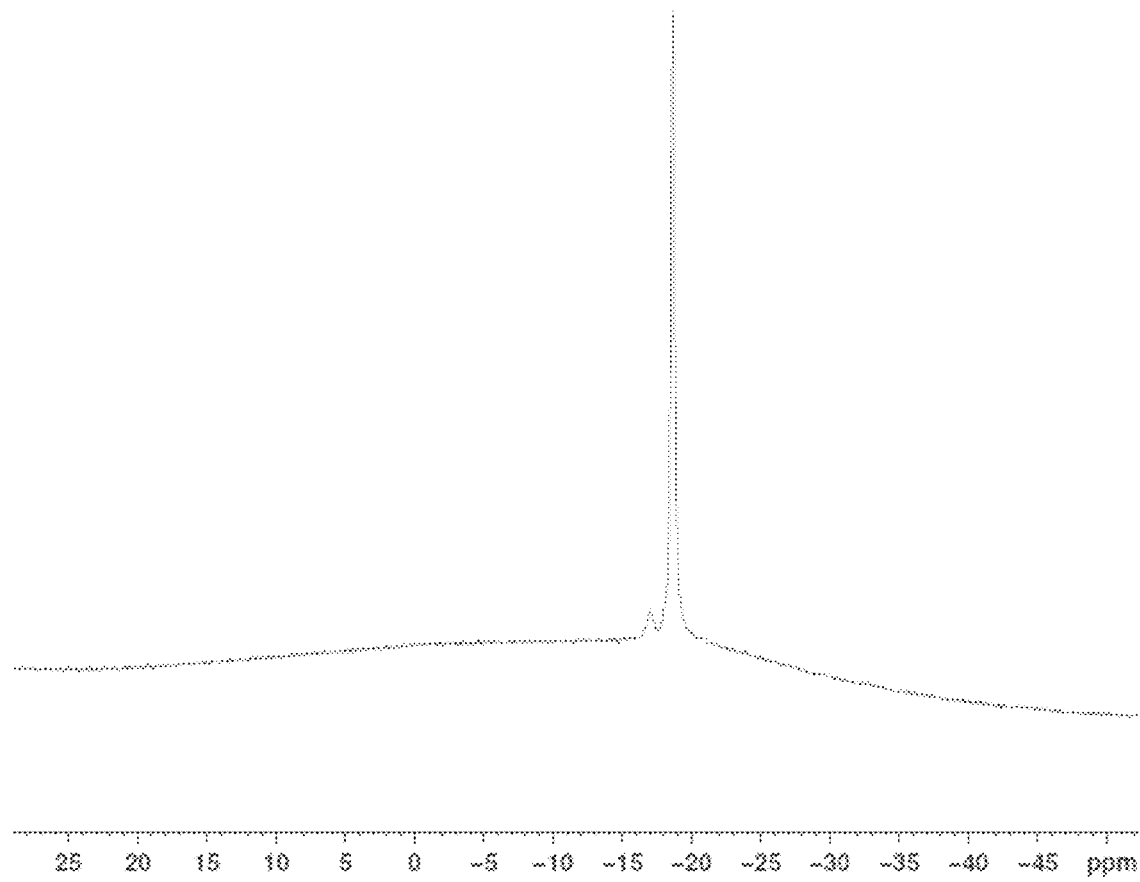
FIG. 7 is the $^{11}B$ NMR of $(n-Bu_4N)_2[closo-B_{12}(OH)_{12}]$.
Figure 8:
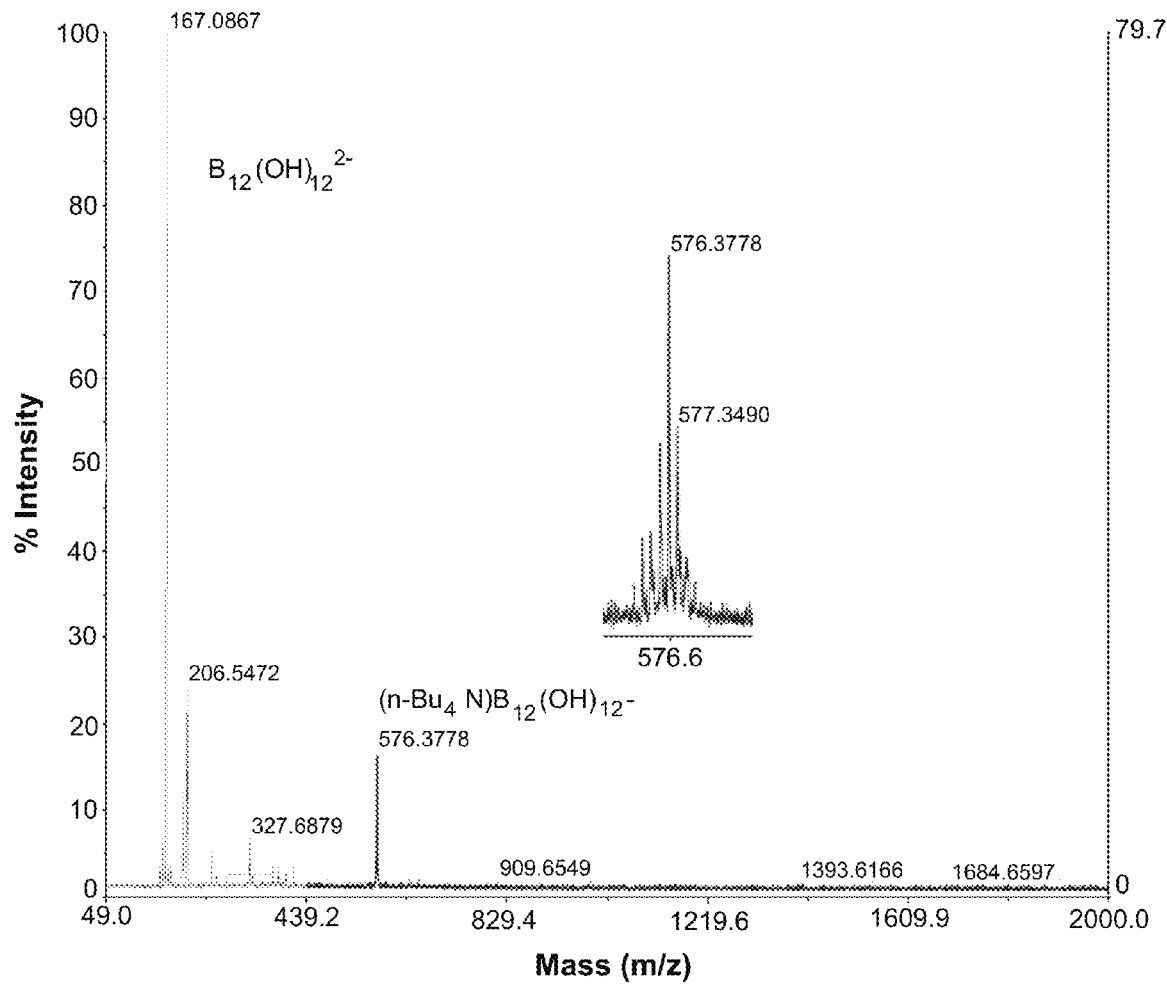
FIG. 8 is the ESI-MS negative ion mass spectrum of $(n-Bu_4N)_2[closo-B_{12}(OH)_{12}]$.
Figure 9:
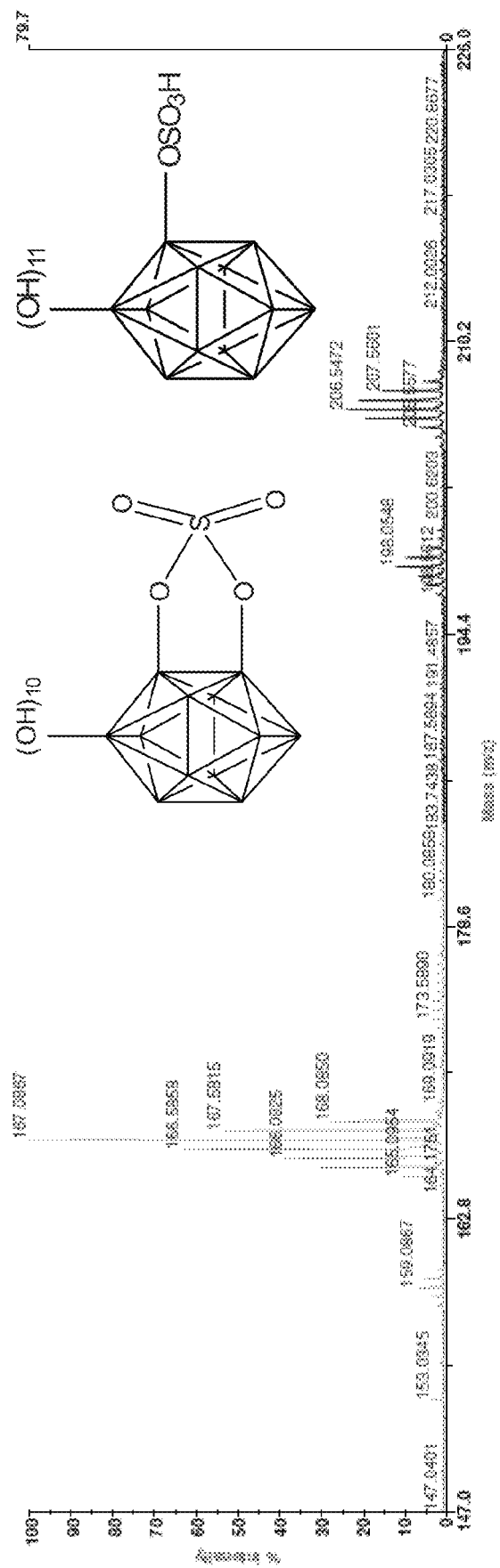
FIG. 9 is the ESI-MS negative ion mass spectrum of $(n-Bu_4N)_2[closo-B_{12}(OH)_{12}]$.
Figure 10:
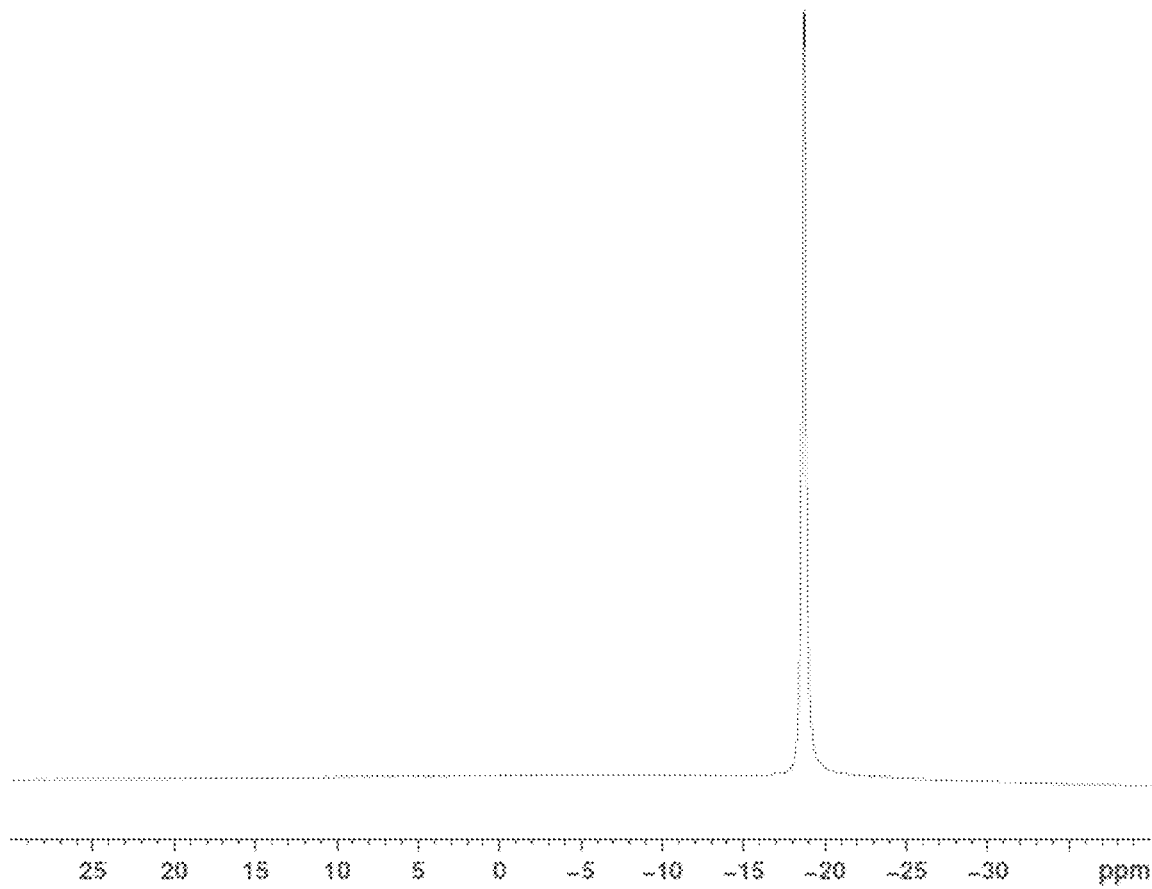
FIG. 10 is the $^{11}B$ NMR of $Cs_2[closo-B_{12}(OH)_{12}]$.
Figure 11:
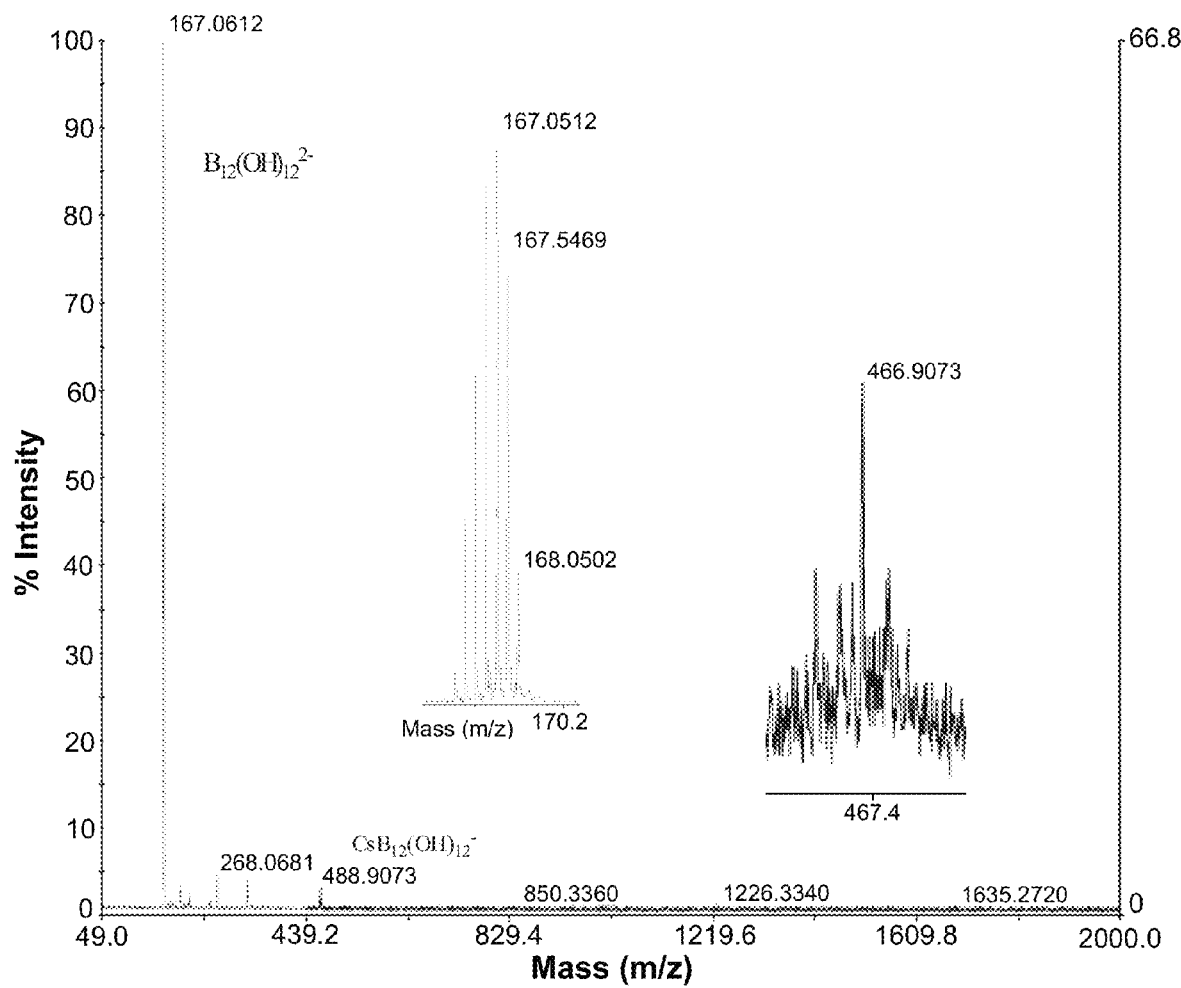
FIG. 11 is the ESI-MS negative ion mass spectrum of $Cs_2[closo-B_{12}(OH)_{12}]$.
Figure 12:
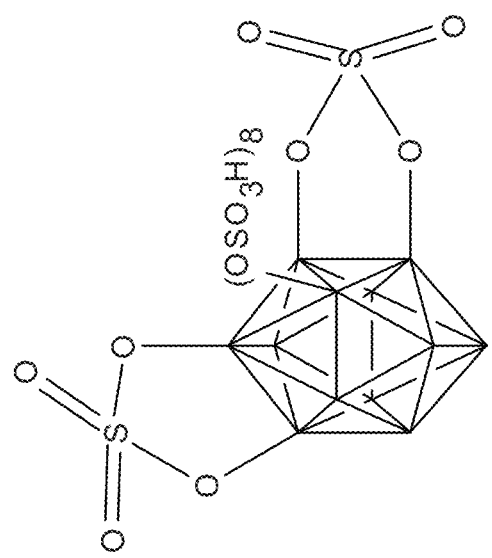
FIG. 12 is a graphic depiction of sulfonated intermediates.
Figure 12:
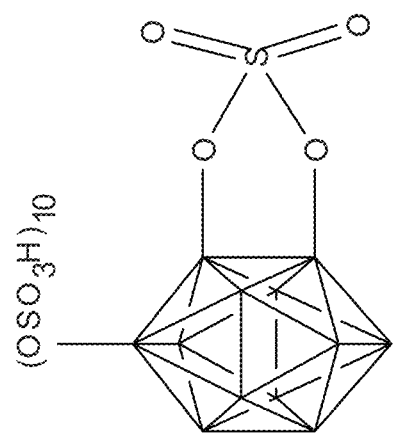
Figure 12:
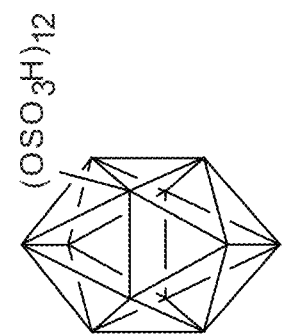

In another aspect of the invention, the per-hydroxylated icosahedral boron compound may be transformed into a stable salt by contacting the per-hydroxylated icosahedral boron compound with the appropriate salt forming compound. In particular, hydroxy or carbonates of Cs or quaternary amines give stable salts. For example, $[closo-B_{12}(OH)_{12}]^{2-}$ can be contacted with AlkOH or $Alk_2CO_3$, wherein Alk is selected from Cs, n-$Bu_4N$, $NH_4$, and $MeNH_3$ as shown in FIG. 4.

In one embodiment, a method of producing a compound $[closo-B_{12}(OH)_{12}]^{2-}$ is provided where the method comprises contacting a compound comprising $[closo-B_{12}H_{12}]^{2-}$ with about 0.5 mol % to about 5 mol % of iodine cation, a palladium species, or a platinum species with sulfuric acid such that a sulfonated intermediate is formed; and hydrolyzing the sulfonated intermediate to give a compound comprising $[closo-B_{12}(OH)_{12}]^{2-}$. The method can be conducted as described in greater detail above.

The yield of the process can and will vary. In some aspects, a yield of 60% or higher of the per-hydroxylated boron compound is given. In other aspects, the yield may be 55%, or 50%, or 45%, or 40%.

(II). Compositions

The invention further provides a sulfonated intermediate. Sulfonated intermediates are given where the icosahedral boron compound is sulfonated at each available position. The sulfonated intermediates may be partially or fully sulfonated, and may be linear or cyclic.

In one aspect, the invention provides a composition comprising $[closo-[closo-B_{12}(OH)_{(12-n)}SO_3R^1)_n]^{2-}$, wherein $R^1$ is chosen from hydrocarbyl, substituted hydrocarbyl, hydrogen, or is not present such that the sulfonated intermediate is anionic, and n is an integer from 1 to 12. In certain embodiments n is 1, 2, 3, 4, 5, 6, 7, 8, 9, 10, 11, or 12. In another aspect, the invention proves a composition comprising $[closo-B_{12}(OSO_3R^1)_{12}]^{2-}$, wherein $R^1$ is hydrogen.

Cyclic sulfonated intermediates may also be present in the composition. In such compositions, the number of hydroxylated and sulfonated positions will depend on whether the sulfur is linear or cyclic. For example, when one sulfonic substitutent is present, eleven hydroxyl groups may be present, but when one cyclic sulfonic substituent is present ten hydroxyl groups may be present. Exemplary compounds in this regard include icosahedral boron compounds having ten or fewer hydroxyl substituents in combination with two or more vertexes being substituted with cyclic sulfate groups.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COON of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "epoxy" or "epoxide" as used herein means a cyclic ether. The ring structure generally comprises from 2 to 5 carbon atoms in the ring.

The terms "halide" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

Materials and Methods $Cs_2[closo-B_{12}H_{12}]$ was purchased from BASF SE. $H_2SO_4$ (fuming, 20% $SO_3$ in $H_2SO_4$) was purchased from Sigma Aldrich (St. Louis, Mo.). Pt(bpym)$Cl_2$ (dichloro-{2,2'- bipyrimidyl}platinum(II)) was synthesized as published. (a) *Inorg. Chem.* 1977, 11, 1280-1284; (b) *Chem. Eur. J.* 2003, 9, 3341-3352; (c) J. Am. Chem. Soc. 2004, 126, 10236-10237]. These publications are incorporated by reference. The $^{11}$B NMR data (160 MHz) were obtained on a Bruker AM-500 spectrometer and referenced to external $BF_3 \times Et_2O$. ESI-mass spectra were recorded by operating in negative-ion mode.

Example 1

Catalytic Experiment 1 ml of $H_2SO_4$ (fuming, 20% $SO_3$ in $H_2SO_4$) was added to a mixture of 50 mg (0.123 mmol) $Cs_2B_{12}H_{12}$ and 2 mg ($4*10^{-3}$ mmol) (4 mol %) Pt(bpym)$Cl_2$. The suspension was heated at 185° C. for 1.5 h, leading to a clear solution. The end of the reaction was monitored by $^{11}$B NMR to 100% conversion. $^{11}$B NMR ($H_2O$): ~18.3 ppm) The obtained solution was poured on 4 g of the ice. Afterwards the solution was diluted with water and neutralized by 6.5 g $Cs_2CO_3$, Finally the solution was evaporated and the product purified by chromatography on a Sephadex® LH-20 column (water as eluent). $^{11}$B NMR ($H_2O$): −16.8 ppm (broad). ESI-mass (m/z): 167.0441 $[B_{12}(OH)_{12}]^{2-}$, 198.0463 $[B_{12}(OH)_{12}(O_2SO_2)]^{2-}$, 229.0499 $[B_{12}(OH)_8(O_2SO_2)(OSO_3H)_3]^{2-}$, 319.5637 $[B_{12}(OH)_7(O_2SO_2)(OSO_3H)_3]^{2-}$, 350.5736 $[B_{12}(OH)_6(O_2SO_2)(OSO_3H)_3]^{2-}$.

Example 2

Catalytic Experiment 2 ml of $H_2SO_4$ (fuming, 20% $SO_3$ in $H_2SO_4$) was added to a mixture of 50 mg (0.123 mmol) $Cs_2B_{12}H_{12}$ and 2 mg ($4*10^{-3}$ mmol) (4 mol %) Pt(bpym)$Cl_2$. The suspension was heated at 185° C. for 2 h, leading to a clear solution. The end of the reaction was monitored by $^{11}$B NMR −100% conversion. $^{11}$B NMR ($H_2O$): −19.0 ppm. The obtained solution was poured on 4 g of the ice. Afterwards the solution was diluted with water and neutralized by 23 ml of n-Bu$_4$NOH (50% solution in water). Finally the solution was evaporated and the product purified by chromatography on a Sephadex® LH-20 column (water as eluent). $^{11}$B NMR ($H_2O$): −18.3 ppm (broad). ESI-mass (m/z): 2327.1$_{12}$1 $[(n-Bu_4N)_5+B_{12}(OH)(O_2SO_2)(OSO_3H)_9]^-$, 2406.4527 $[(n-Bu_4N)_5+B_{12}(O_2SO_2)(OSO_3H)_{10}]$.

Example 3

Low Temperature Experiment 2 ml of $H_2SO_4$ (fuming, 20% $SO_3$ in $H_2SO_4$) was added to a mixture of 50 mg (0.123 mmol) $Cs_2B_{12}H_{12}$ and 2 mg ($4*10$-3 mmol) (4 mol %) Pt(bpym)$Cl_2$. The suspension was heated at 120° C. for 3 days, leading to a clear solution. The end of the reaction was monitored by $^{11}$B NMR. After 3 days the reaction was complete. $^{11}$B NMR ($H_2O$): −18.6 ppm.

Example 4

Blank Experiment 1 ml of $H_2SO_4$ (fuming) was added to 50 mg (0.123 mmol) $Cs_2B_{12}H_{12}$. The suspension was heated at 185° C. for 60 hours, leading to a clear solution. The $^{11}$B NMR showed peaks: −13.8 ppm; −30.2 ppm (ratio 1/1) corresponding $[B_{12}H_{12-n}(OH)_n]^{2-}$.

Example 5

Blank Experiment 1 ml of $H_2SO_4$ (98% conc.) was added to a mixture of 50 mg (0.123 mmol) $Cs_2B_{12}H_{12}$ and 2 mg ($4*10^{-3}$ mmol) (4 mol %) Pt(bpym)$Cl_2$. The suspension was heated at 185° C. for 60 hours, leading to a clear solution. The $^{11}$B NMR showed peaks: −11.0 ppm; −27.8 ppm (ratio 1/1), corresponding $[B_{12}H_{12-n}(OH)_n]^{2-}$.

Example 6

Blank Experiment 2 ml of $H_2SO_4$ (64% conc. $H_2SO_4$ in water) was added to mixture of 50 mg (0.123 mmol) $Cs_2B_{12}H_{12}$ and 2 mg ($4*10^{-3}$ mmol) (4 mol %) Pt(bpym)$Cl_2$, The suspension was heated at 185° C. for 60 hours, leading to a clear solution. The $^{11}$B NMR showed peaks: −12.6 ppm; −29.7 ppm (ratio 1/1), corresponding $[B_{12}H_{12-n}(OH)_n]^{2-}$.

Example 7

Hydrolysis

To 0.5 g $[n-Bu_4N]_2B_{12}(OR^1)_{12}$, where $R^1=SO_3H$, was added 2 ml HCl (35% conc.) and refluxed for 4 days. A colorless precipitate formed after 1 day of reaction. The precipitated solid was collected by filtration and recrystallized from water to yield 50 mg (0.135 mmol, 48% yield) of $(H_3O)_2B_{12}(OH)_{12}$. The product was suspended in water, and an aqueous n-Bu$_4$NOH solution was added until the solution was neutral. Removal of the solvent under reduced pressure yielded $[n-Bu_4N_{12}B_{12}(OH)_{12}$ as a white solid (110 mg, 99% yield). $^{11}$B NMR ($H_2O$): 18.7 ppm. ESI-mass (m/z): 334.1500 $[H+B_{12}(OH)_{12}]$—, 576.4219 $[NBu_4+B_{12}(OH)_{12}]^-$. Some $[n-Bu_4N]_2B_{12}(OH)_{10}(O_2SO_2)$ and $[n-Bu_4N]_2B_{12}(OH)_{11} OSO_3H$ are presented in ESI-mass as by-products.

Example 8

One-Pot Reaction 10 ml of $H_2SO_4$ (fuming, 20% $SO_3$ in $H_2SO_4$) was added to a mixture of 0.5 g (1.23 mmol) $Cs_2B_{12}H_{12}$ and 20 mg (0.04 mmol) (4 mol %) Pt(bpym)$Cl_2$. The suspension was heated at 185° C. for 18 h, leading to a clear solution. The obtained solution was poured on ice. The solution was diluted with 25 ml of water and refluxed for 4 days. A colorless precipitate was formed after 1 day of hydrolysis. The precipitated solid was collected by filtration and recrystallized from water to yield 192 mg (0.516 mmol, 42% yield) of $(H_3O)_2B_{12}(014)_{12}$. After that, the product was suspended in water and aqueous $CsCO_3$ solution was added until the solution was neutral. The hydronium salt dissolved during this step in the process. The solution was concentrated by evaporation until crystals of $Cs_2B_{12}(OH)_{12}$ appeared. Finally the solid crystals $Cs_2B_{12}(OH)_{12}$ were separated and recrystallized twice from water (37 mg, 12% yield). Alternatively 2 ml of $H_2O_2$ (30% conc. in water) was added to 300 mg of $Cs_2B_{12}(OH)_{12}$ which contained 6% impurity of $Cs_2B_{12}(OH)_{11}OSO_3H$, then heated at the reflux temperature for 12 h. The resulting solution was cooled in a refrigerator and the obtained precipitate was recrystallized from water (195 mg, 65% yield). $^{11}$B NMR ($H_2O$): −18.0 ppm. ESI-mass (m/z): 333.0666 [H+$B_{12}$(OH)$_{12}$], 466.9073 [Cs+$B_{12}$(OH)$_{12}$].

Example 9

One-Pot Reaction 10 ml of $H_2SO_4$ (fuming, 20% $SO_3$ in $H_2SO_4$) was added to a mixture of 0.5 g (1.23 mmol) $Cs_2B_{12}H_{12}$ and 19 mg (0.06 mmol) (5 mol %) Pt(NH$_3$)$_2$Cl$_2$. The suspension was heated at 195° C. for 18 h, leading to a clear solution. The obtained solution was poured on ice. Afterwards the solution was diluted with 25 ml of water and refluxed for 3 days. The precipitated solid was collected by filtration and recrystallized from water to yield 238 mg (0.639 mmol, 52% yield) of ($H_3O$)$_2B_{12}$(OH)$_{12}$. $^{11}$B NMR ($H_2O$): −18.0 ppm.

Example 10

One-Pot Reaction 15 ml of $H_2SO_4$ (fuming, 20% $SO_3$ in $H_2SO_4$) was added to a mixture of 1 g (2.46 mmol) $Cs_2B_{12}H_{12}$ and 623 mg (1.23 mmol) (1 eq) $J_2$. The suspension was heated at 195° C. for 18 h, leading to a clear solution. The obtained solution was poured on ice. Insoluble in water, the iodine was filtered off. The solution was diluted with 30 ml of water and refluxed for 3 days. The precipitated solid was collected by filtration and recrystallized from water to yield 384 mg (1.03 mmol, 42% yield) of ($H_3O$)$_2B_{12}$(OH)$_{12}$. $^{11}$B NMR ($H_2O$): −18.0 ppm.

Example 11

One-Pot Reaction 30 ml of $H_2SO_4$ (fuming, 20% $SO_3$ in $H_2SO_4$) was added to a mixture of 2 g (4.93 mmol) $Cs_2B_{12}H_{12}$ and 88 mg (0.5 mmol) (10 mol %) PdCl$_2$. The suspension was heated at 195° C. for 72 h, leading to a clear solution. The obtained solution was poured on ice. The solution was diluted with 70 ml of water and refluxed for 3 days. The precipitated solid was collected by filtration and recrystallized from water to yield 879 mg (2.35 mmol, 48% yield) of ($H_3O$)$_2B_{12}$(OH)$_{12}$. $^{11}$B NMR ($H_2O$): −18.0 ppm.

Example 12

Hydrolysis in Autoclave 5 ml of $H_2SO_4$ (fuming, 20% $SO_3$ in $H_2SO_4$) was added to a mixture of 0.25 g (0.62 mmol) $Cs_2B_{12}H_{12}$ and 5 mg (0.03 mmol) (5 mol %) PdCl$_2$. The suspension was heated at 195° C. for 18 h, leading to a clear solution. The obtained solution was poured on 5 g of ice. The solution was diluted with 5 ml of water and transferred into a glass-autoclave. The autoclave was heated to 200° C. for 24 h. After that, the autoclave was cooled to room temperature and depressurized. The precipitated solid was collected by filtration and recrystallized from water to yield 110 mg (0.296 mmol, 48% yield) of ($H_3O$)$_2B_{12}$(OH)$_{12}$. $^{11}$B NMR ($H_2O$): −18.0 ppm.

Example 13

Cs$_2$[closo-B$_{12}$(OH)$_{12}$] Synthesis

Cautiously, 10 ml of $H_2SO_4$ (fuming, 20% $SO_3$ in $H_2SO_4$) was added to a mixture of 0.50 g (1.2 mmol) Cs$_2$[closo-B$_{12}$H$_{12}$] and 20 mg (0.04 mmol) (4 mol %) [Pt(bpym)]Cl$_2$. The suspension was heated at 185° C. for 18 h, leading to a clear solution, which was cooled and then poured on ice. The resulting solution was diluted with 25 ml of water and heated at reflux for 4 days. A colorless precipitate was seen after 1 day of hydrolysis. The precipitated solid was collected by filtration and recrystallized from water to yield 192 mg (0.52 mmol, 42% yield) of ($H_3O$)$_2$[closo-B$_{12}$(OH)$_{12}$]. This hydronium ion salt was then suspended in water, and aqueous Cs$_2$CO$_3$ solution was added until the solution was neutral. The resulting solution was concentrated by evaporation until crystals of Cs$_2$[closo-B$_{12}$(OH)$_{12}$] appeared. Finally the solid crystals Cs$_2$[closo-B$_{12}$(OH)$_{12}$] were separated and recrystallized twice from water. The $^{11}$B NMR data (160 MHz) were obtained on a Bruker AM-500 spectrometer and referenced to external BF$_3$×Et$_2$O. Mass spectra were obtained on Mariner Biospectrometry Workstation by PerSeptive Biosystems. ESI-mass spectra were recorded by operating in negative-ion mode.

Example 14

Synthesis of ($H_3O$)$_2$[closo-B$_{12}$(OH)$_{12}$]

Cautiously, 30 ml of $H_2SO_4$ (fuming, 20% $SO_3$ in $H_2SO_4$) was added to a mixture of 2.0 g (4.9 mmol) Cs$_2$[closo-B$_{12}$H$_{12}$] and 88 mg (0.50 mmol) (10 mol %) [PdCl$_2$]. The suspension was heated at 195° C. for 72 h, leading to a clear solution. The progress of the reaction was monitored by $^{11}$B NMR. The reaction solution was poured on ice. The solution was diluted with 70 ml of water and heated at reflux for 3 days. The precipitated solid was collected by filtration and recrystallized from water to yield 880 mg (2.4 mmol, 48% yield) of ($H_3O$)$_2$[closo-B$_{12}$(OH)$_{12}$]. $^{11}$B NMR ($H_2O$): −18.7 ppm. The $^{11}$B NMR data (160 MHz) were obtained on a Bruker AM-500 spectrometer and referenced to external BF$_3$×Et$_2$O. Mass spectra were obtained on Mariner Biospectrometry Workstation by PerSeptive Biosystems. ESI-mass spectra were recorded by operating in negative-ion mode.

While the invention has been described in connection with specific embodiments thereof, it will be understood that the inventive device is capable of further modifications.

What is claimed is:

1. A method of producing a per-hydroxylated icosahedral boron compound, the method comprising the steps of:
   (a) contacting an icosahedral boron compound with a soft electrophile and a sulfonic acid such that a sulfonated intermediate is formed; and
   (b) hydrolyzing the sulfonated intermediate to give the per-hydroxylated icosahedral boron compound.

2. The method of claim 1, wherein the icosahedral boron compound comprises [closo-B$_{12}$H$_{12}$]$^{2-}$ and the per-hydroxylated boron compound comprises [closo-B$_{12}$(OH)$_{12}$]$^{2-}$.

3. The method of claim 2, wherein the soft electrophile is a platinum species, a palladium species, or an iodine species.

4. The method of claim 2, wherein the soft electrophile is Pt(bpym)Cl$_2$.

5. The method of claim 2, wherein the soft electrophile is Pt(NH$_3$)$_2$Cl$_2$.

6. The method of claim 2, wherein the soft electrophile is PdCl$_2$.

7. The method of claim 2, wherein the soft electrophile is iodine cation.

8. The method of claim 2, wherein the soft electrophile is added in an amount ranging from about 0.5 mol % to about 5 mol % to the [closo-B$_{12}$H$_{12}$]$^{2-}$.

9. The method of claim 2, wherein step (a) is conducted at a temperature ranging from about 160° C. to about 200° C.

10. The method of claim 2, wherein step (a) is conducted over a period of about 18 hours.

11. The method of claim 2, wherein step (b) comprises an acid hydrolysis.

12. The method of claim 2, wherein step (b) comprises addition of water.

13. The method of claim 2, the method further comprising formation of an alkali boron by contacting the compound comprising [closo-$B_{12}(OH)_{12}$]$^{2-}$ with an alkali carbonate or alkanol.

14. The method of claim 2, wherein step (a) is conducted in the absence of hydrogen peroxide or a reactive oxygen species.

15. The method of claim 2, wherein the reaction is conducted in one pot.

16. A composition comprising [closo-$B_{12}(OSO_3R^1)_{12}$]$^{2-}$, wherein $R^1$ is hydrocarbyl, substituted hydrocarbyl, hydrogen, or is not present such that the sulfonated intermediate is anionic.

17. The composition of claim 16, wherein $R^1$ is hydrogen.

18. A method of producing a compound comprising [closo-$B_{12}(OH)_{12}$]$^{2-}$, the method comprising the steps of:

(a) contacting a compound comprising [closo-$B_{12}H_{12}$]$^{2-}$ with about 0.5 mol % to about 5 mol % of a soft electrophile selected from a group consisting of a palladium species, a platinum species, and an iodine species, and with sulfuric acid such that a sulfonated intermediate is formed; and (b) hydrolyzing the sulfonated intermediate to give the compound comprising [closo-$B_{12}(OH)_{12}$]$^{2-}$.

19. The method of claim 18, wherein the platinum species is Pt(bpym)$Cl_2$.

20. The method of claim 18, wherein the platinum species is Pt(NH$_3$)$_2$Cl$_2$.

21. The method of claim 18, wherein the palladium species is PdCl$_2$.

22. The method of claim 18, wherein the iodine species is iodine cation.

23. The method of claim 18, wherein step (a) is conducted at a temperature ranging from about 160° C. to about 200° C.

24. The method of claim 18, wherein step (b) comprises an acid hydrolysis.

25. The method of claim 18, wherein step (b) comprises addition of water.

* * * * *